(12) United States Patent
Bewlay et al.

(10) Patent No.: US 6,596,099 B2
(45) Date of Patent: Jul. 22, 2003

(54) TITANIUM ARTICLES AND STRUCTURES FOR ULTRASONIC INSPECTION METHODS AND SYSTEMS

(75) Inventors: Bernard Patrick Bewlay, Schenectady, NY (US); John Broddus Deaton, Jr., Niskayuna, NY (US); Michael Francis Xavier Gigliotti, Jr., Scotia, NY (US); Robert Snee Gilmore, Charlton, NY (US)

(73) Assignee: General Electric Company, Niskayuna, NY (US)

( * ) Notice: Subject to any disclaimer, the term of this patent is extended or adjusted under 35 U.S.C. 154(b) by 14 days.

(21) Appl. No.: 09/833,841

(22) Filed: Apr. 12, 2001

(65) Prior Publication Data

US 2002/0043315 A1 Apr. 18, 2002

Related U.S. Application Data

(63) Continuation of application No. 09/454,188, filed on Dec. 3, 1999, now Pat. No. 6,370,956.

(51) Int. Cl.[7] .............................. C22C 14/00; C22F 1/18
(52) U.S. Cl. ........................ 148/421; 148/670; 148/671
(58) Field of Search ................................ 148/421, 670, 148/671

(56) References Cited

U.S. PATENT DOCUMENTS

| | | | | |
|---|---|---|---|---|
| 5,039,356 A | * | 8/1991 | Weiss et al. | 148/691 |
| 5,277,718 A | * | 1/1994 | Paxson et al. | 148/671 |
| 5,445,688 A | * | 8/1995 | Gigliotti, Jr. et al. | 148/527 |
| 6,190,473 B1 | * | 2/2001 | Martin | 148/671 |
| 6,370,956 B1 | * | 4/2002 | Bewlay et al. | 73/99 |
| 6,387,197 B1 | * | 5/2002 | Bewlay et al. | 148/669 |

FOREIGN PATENT DOCUMENTS

EP        1 136 582        9/2001

OTHER PUBLICATIONS

"The Case of the Missing Ultrasound", http://www.classic-medical.com/review/tcmu.html, accessed on Oct. 24, 2002.*
"Heat Treating of Titanium and Titanium Alloys", from ASM Handbook vol. 4, pub. by ASM International, 1991, pp. 913–919.*
ASM Handbook vol. 2 "Properties and Selection: Nonferrous Alloys and Special–Purpose Materials", pub. by ASM International, 1990, pp. 600, 601, 603, 614, 620.*
The Journal of The Acoustical Society of America, Revised Grain–Scattering Formulas and Tables, Emmanuel P. Papadakis, vol. 37, No. 4, pp. 703–710, Apr. 1965.
The Journal of The Acoustical Society of America, Ultrasonic Attenuation Caused by Scattering in Polycrystalline Metals, Emmanuel P. Papadakis, vol. 37, No. 4, pp. 711–717, Apr. 1965.

* cited by examiner

Primary Examiner—Roy King
Assistant Examiner—Harry D. Wilkins, III
(74) Attorney, Agent, or Firm—Robert P. Santandrea; Noreen C. Johnson

(57) ABSTRACT

A titanium article for an ultrasonic inspection is provided in which the titanium article can be ultrasonic inspected for determining its acceptability in for microstructurally sensitive applications. The ultrasonic inspection method comprises providing a titanium article, directing ultrasonic energy of ultrasonic inspection to the titanium article; scattering reflected energy in the titanium article; determining an amount of noise generated by the ultrasonic inspection of the titanium article; and characterizing the titanium article as acceptable if the amount of noise as a function of ultrasonic frequency or wavelength is characteristic of predominantly Rayleigh scattering and the magnitude of the noise is less than a pre-determined noise level. The titanium article comprises an uniform-fine grain microstructure. The uniform-fine grain microstructure generates predominantly Rayleigh scattering when undergoing ultrasonic inspection. The invention also sets forth a method of forming a titanium article. The method of forming comprises providing a uniform fine grain titanium material by a processes selected from forging and heat treating a billet of conventional titanium material into the titanium article.

24 Claims, 8 Drawing Sheets

(a)

(b)

(c)

(d)

TITANIUM ARTICLES AND STRUCTURES FOR ULTRASONIC INSPECTION METHODS AND SYSTEMS

This application is a continuation of application Ser. No. 09/454,188, filed Dec. 3, 1999, now U.S. Pat. No. 6,370,956, which is hereby incorporated by reference in its entirety.

BACKGROUND OF THE INVENTION

The invention relates to titanium articles and structures for inspection methods and systems. In particular, the invention relates to inspecting titanium articles and structures using ultrasonic energy inspection methods and systems.

Nondestructive evaluation of articles and structures by ultrasonic inspection and ultrasonic inspection testing is a known testing and evaluation method. Ultrasonic testing typically requires that detectable flaws in the articles and structures possess different acoustic behaviors from bulk material articles and structures undergoing similar ultrasonic inspection. This different behavior permits the ultrasonic inspection to detect flaws, grains, imperfections, and other related microstructural characteristics for a material.

Materials forming articles and structures with large, elastically anisotropic grains, such as, but not limited to, cast ingots of steels, titanium alloys, and nickel alloys, are often difficult to evaluate by ultrasonic testing. The difficulties arise, at least in part to, because sound waves, which are used for ultrasonic inspection, are reflected from grains and grain arrays sharing common elastic behavior, and represent a background "noise." The generated background noise can mask flaws in the material, and is thus undesirable.

Ultrasonic inspection techniques have been developed that use focused ultrasonic beams to enhance a flaw fraction within any instantaneously insonified volume of material in articles and structures. These developed ultrasonic inspection techniques can identify indications based both on maximum signal, as well as signal to noise. A scattering of sound in a polycrystalline metallic material body, which is also known in the art as an attenuation of a propagating sound wave, can be described as a function of at least one of grain dimensions, intrinsic material characteristics, and ultrasound frequency. Typically, three different functional relationships among scattering, frequency, and grain dimensions have been described. These are:

for $\lambda > 2\pi D$, $\alpha = Tv^4\Theta$), termed "Rayleigh" scattering;

for $\lambda < 2\pi D$ or $\lambda \approx D$, $\alpha = Dv^2\Sigma$, termed "stochastic" or "phase" scattering; and for $\lambda << D$, $\alpha$ 1/D, termed "diffusion" scattering;

where $\alpha$ is attenuation, $\lambda$ is wavelength of the ultrasound energy, $v$ is frequency of the ultrasound energy, D is an average grain diameter, T is a scattering volume of grains, and $\Theta$ and $\Sigma$ are scattering factors based on elastic properties of the material being inspected.

The microstructure of a material in articles and structures can determine the applications in which the articles and structures can be used, and the microstructure of a material can limit the applications in which the material can be used. The microstructure can be determined by measuring the scattering of sound in a material. The scattering of sound in a material, such as titanium, may be sensitive to its microstructure. The titanium microstructure's sound scattering sensitivity can be attributed to αTi particles that are arranged into "colonies." These colonies typically have a common crystallographic (and elastic) orientation, and these colonies of αTi particles can behave as large grains in the titanium material. An individual αTi particle might be about 5 μm in diameter, however, a colony of αTi particles could be greater than about 200 μm in diameter. Thus, the size contribution attributed to sound scattering sensitivity from αTi particles could vary over 40-fold among differing microstructures. Additionally, the sound scattering sensitivity due to αTi particles could change between that from randomly crystallographically oriented αTi particles to that from αTi particles within crystallographically oriented colonies of αTi particles.

Colony structures are formed during cooling a titanium alloy from a high temperature as βTi transforms to αTi. There is a crystallographic relation between the αTi and the parent βTi grain, such that there are only three crystallographic orientations that αTi will take forming from a given βTi grain. If the cooling rate is high and there is uniform nucleation of αTi throughout the grain, neighboring αTi particles have different orientations, and each behave as a distinct acoustic scattering entity. However, if there are only a few sites of αTi nucleation within the βTi grain, then the αTi particles in a given area all grow with the same orientation, and a colony structure results. This colony becomes the acoustic entity. Since a colony is formed within a βTi grain, the colony size will be less than the βTi grain size. The size of βTi grains and the nature of αTi particles colony structures may be important variables that influence ultrasonic noise and ultrasonic inspection in single phase and two-phase titanium alloys and materials. Therefore, the size of βTi grains and the nature of αTi particles in colony structures may influence ultrasonic inspection techniques, methods, and results by creating undesirable noise during ultrasonic inspection. While thermomechanical processing techniques, which rely on dynamic recrystallization in the α+β temperature range to achieve uniform fine grain (UFG) αTi particles and prevent colony formation, have been developed to improve titanium microstructure, defects may remain in the titanium material. These defects may be undesirable for some titanium material applications.

While ultrasonic inspection of most articles can be preformed with some degree of certainty, the shape, size, configuration, structure, and orientation of the articles and structures undergoing ultrasonic inspection may impair the ultrasonic inspection. There are shapes, sizes, configurations, structures, and orientations of some articles and structures that may enhance the ultrasonic inspection. Thus, in order to have acceptable titanium for certain applications, it is desirable to provide titanium articles and structures for ultrasonic inspection that enhances the ultrasonic inspection and can assist in the determination and differentiation of noise during ultrasonic inspection. Thus, with certain titanium articles and structures ultrasonic inspection method should be able to determine if ultrasonic inspection noise is attributed to a defect in the titanium material, or is due to other factors.

Therefore, a need exists for providing titanium articles and structures for ultrasonic inspection methods for enhancing accurate determinations of material characteristics and properties. Further, a need exists for providing titanium articles and structures for ultrasonic inspection for enhancing accurate determinations of processed titanium characteristics and properties.

SUMMARY OF THE INVENTION

In one aspect of the invention, a titanium article for an ultrasonic inspection is provided. The titanium article can be ultrasonically inspected for determining its acceptability in for microstructurally sensitive applications. The ultrasonic inspection method comprises providing a titanium article, directing ultrasonic energy of ultrasonic inspection to the titanium article; scattering reflected energy in the titanium article; determining an amount of noise generated by the ultrasonic inspection of the titanium article; and characterizing the titanium article as acceptable if the amount of noise as a function of ultrasonic frequency or wavelength is characteristic of predominantly Rayleigh scattering, which means that the Rayleigh scattering comprises at least a majority of the scattering and dominates other types of scattering, and the magnitude of the noise is less than a pre-determined noise level. The titanium article comprises an uniform-fine grain microstructure. The uniform-fine grain microstructure generates predominantly Rayleigh scattering when undergoing ultrasonic inspection.

The invention also sets forth a method for forming a titanium article for an ultrasonic inspection. The ultrasonic inspection method is capable of determining acceptability of the titanium article for microstructurally sensitive applications in which the method comprises providing a titanium article, directing ultrasonic energy of ultrasonic inspection to the titanium article; scattering reflected energy in the titanium article; determining an amount of noise generated by the ultrasonic inspection of the titanium article; and characterizing the titanium article as acceptable if the amount of noise as a function of ultrasonic frequency or wavelength is characteristic of predominantly Rayleigh scattering and the magnitude of the noise is less than a predetermined noise level. The method of forming comprises providing a uniform fine grain titanium material by a processes selected from forging and heat treating a billet of conventional titanium material into the titanium article.

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

Figure 1:
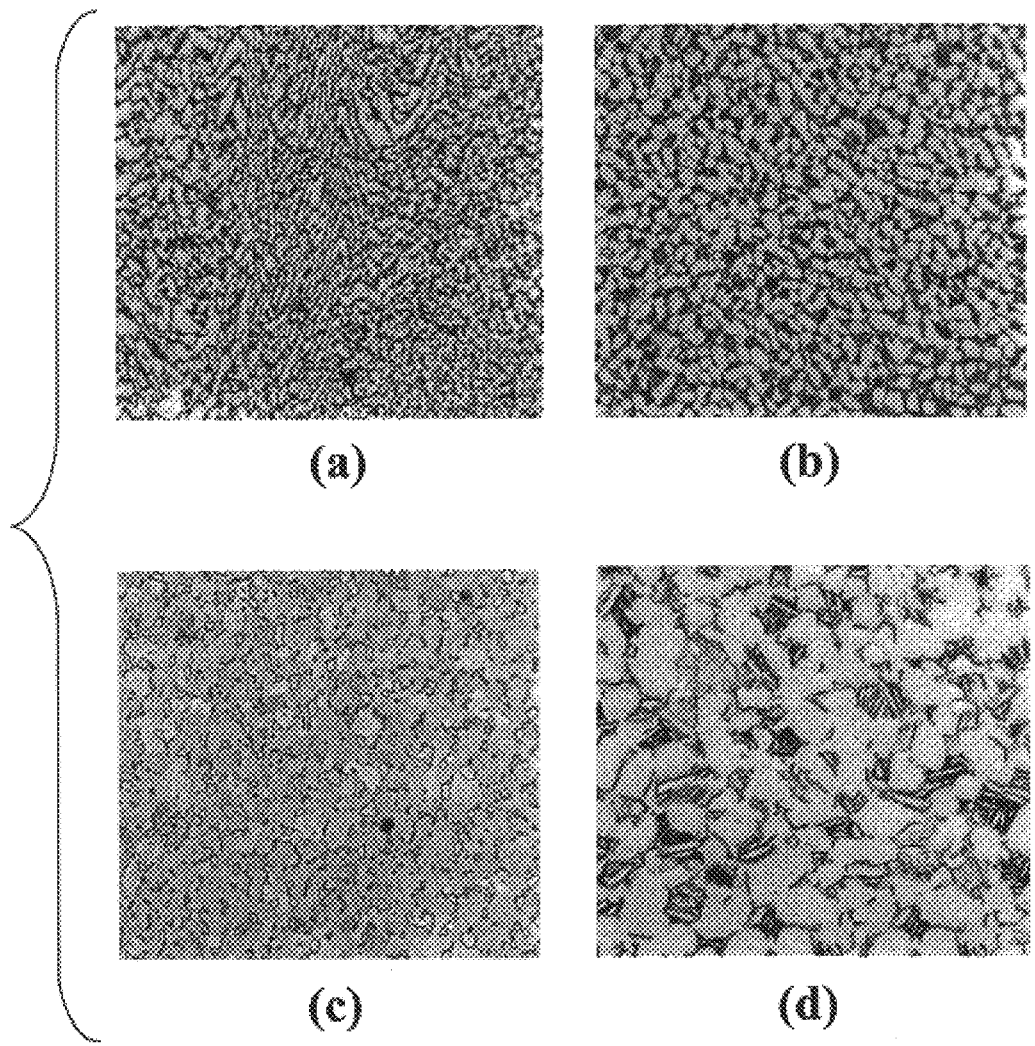
FIG. 1 illustrates light micrographs of Ti6242 material that in the following conditions: (a) conventional billet; (b) conventional forging; (c) uniform fine grain (UFG) billet; (d) a forging of a UFG billet.

The titanium articles and structures, as embodied by the invention, provide titanium articles and structures for ultrasonic inspection methods and systems. The titanium articles and structures, as embodied by the invention, that are inspected can be used to determine if the titanium microstructures comprise fine-scale granular αTi particles. Also, the titanium articles and structures, as embodied by the invention, provide titanium articles and structures for ultrasonic inspection with enhanced determinations and indications of uniform-fine grain (UFG) billets and forgings made from UFG billets. Also, the titanium articles and structures, as embodied by the invention, provide titanium articles and structures for ultrasonic inspection, in which the titanium articles and structures generally generate predominantly Rayleigh scattering, which is indicative of uniform-fine grain microstructure. The functionality of scattering as a function of acoustic entity size and ultrasound wavelength varies in a smooth fashion from one regime ("Rayleigh" to "phase" to "diffusion") to another. For adequate inspection to find critical flaws, and to assure predominantly Rayleigh scattering, the acoustic entity size needs to be not greater than about 1/10 the wavelength of the sound used for inspection.

The generated Rayleigh scattering from titanium articles and structures, as embodied by the invention, is typically indicative that the titanium articles and structures comprise uniform-fine grains (UFG). Thus, the titanium articles and structures are suitable for various microstructurally sensitive applications, such as but not limited to turbine components. Therefore, using the titanium articles and structures, as embodied by the invention, for ultrasonic inspection will enhance the results of ultrasonic inspection, because UFG titanium microstructures generate predominantly Rayleigh scattering. If the ultrasonic inspection determines scattering other than predominantly Rayleigh scattering, for example phase scattering alone or in combination with Rayleigh scattering, it is possible to characterize the titanium articles and structures as not comprising uniform-fine grain titanium.

αTi particles are generally less than about 5 μm in diameter, and are generally formed with an absence of crystallographic texture. The ultrasonic inspectability of these UFG titanium materials is characterized by a signal to noise ratio from machined flat bottom holes. The signal to noise ratio obtained by ultrasonic inspection is greater in UFG titanium materials than in the conventional titanium materials. It has been determined that there is less ultrasonic backscattered noise in the UFG titanium materials than in the conventional titanium materials. Further, it has been determined using ultrasonic inspection of titanium articles and structures that an ultrasonic signal from machined flat-bottomed holes is higher in the UFG titanium material.

Further, the ultrasonic inspection of titanium articles and structures indicates that the presence of a αTi particle colony structure is associated with ultrasonic noise. For titanium materials with αTi particles less than about 10 μm in size, differences in αTi particle size typically do not have a significant effect on generated ultrasonic noise. For example, UFG billets display chiefly Rayleigh scattering, while conventional billets, which are not be characterized by UFG properties, display Rayleigh scattering plus phase scattering when subjected to ultrasonic inspection. Therefore, as embodied by the invention, the inspectability of titanium-containing materials is enhanced using titanium articles and structures that generate predominantly Rayleigh scattering.

The titanium articles and structures, as embodied by the invention, for ultrasonic inspection comprise UFG microstructural characteristics and features that can be determined using the titanium article's sound scattering sensitivity. The ultrasonic inspection method comprises providing a titanium articles and structures, as embodied by the invention, for example a Ti6242 alloy. This Ti6242 alloy material is merely exemplary of the titanium materials for titanium articles and structures within the scope of the invention. The description of a Ti6242 alloy for the titanium articles and structures is in no way intended to limit the scope of the invention.

The titanium articles and structures (or "titanium material") is subjected to ultrasonic inspection by directing ultrasonic energy onto the titanium material. The ultrasonic energy directed into the material typically comprises a pulse of sound at a selected frequency. The sound pulse is scattered in a manner determined by the frequency of the sound pulse, the microstructural features of the titanium material, and by intrinsic physical characteristics, such as but not limited to, elastic constants and mass density, of the titanium material. The scattered energy is then analyzed and a determination of the characteristics of the scattered noise is made with regard to the nature of the scattering for the titanium articles and structures.

The titanium material for ultrasonic inspection comprises a uniform fine grain (UFG) material, which can be produced by forging a billet of conventional titanium material into various and appropriate structures, configurations, and shapes, as embodied by the invention. For example, the UFG titanium articles and structures can be formed by steps of press forging, heat-treating, quenching, and subsequent cooling. The titanium that is actually subjected to the ultrasonic inspection, as embodied by the invention, may be further prepared by providing a titanium billet with at least one, for example a series, of flat bottom holes. These flat bottom holes will serve as pixel intensity standards, upon which the ultrasonic inspection can be gauged.

A signal to noise ratio for synthetic flaws machined in the Ti6242 blocks is strongly influenced by titanium microstructural condition, for example as the Ti6242 is defined by electron backscatter diffraction analysis. Ti6242 blocks having a microstructure comprising uniform, fine, texture-free αTi particles typically provided signal to noise ratios about 20 dB greater than similar titanium blocks with microstructures having colonies comprising crystallographically aligned αTi particles.

The ultrasonic inspection method and procedure will now be described with reference to titanium articles and structures and titanium materials, as embodied by the invention. In the following discussion, the terms are used with their normal meanings as understood by person of ordinary skill in the art, unless discussed to the contrary. Further, the dimensions are approximate, unless stated to be exact.

The ultrasonic inspection provides titanium articles and structures, such as a Ti6242 alloy, for evaluation. The Ti6242 material is evaluated when the titanium material has been configured into four microstructural conditions: a conventional billet; a conventional forging from conventional billet; a uniform fine grain (UFG) billet; and a forging of the UFG billet. The individual billets will be referred to by the above names, and collectively as "billets".

The conventional billet is about 23 centimeters (cm) (9 inch) in diameter. The conventional forging is from the bore region of a disk forging, for example a compressor disk forging. The UFG billet is produced as two bars from about 10 cm×10 cm×20 cm sections taken from the commercial billet and having its grain refined under accepted titanium alloy grain refinement processes. The forging of UFG billet is produced by press forging at temperatures of about 900° C. about a 7 cm tall, 6.35 cm diameter cylinder of the UFG billet to about a 2.80 cm final height at 2.5 cm/min pressing speed. The forging of UFG billet is given a heat treatment of about 970° C., for about 1 hour, followed by a helium quench, at about 705° C., for about 8 hours, followed by an air cool.

Figure 2:
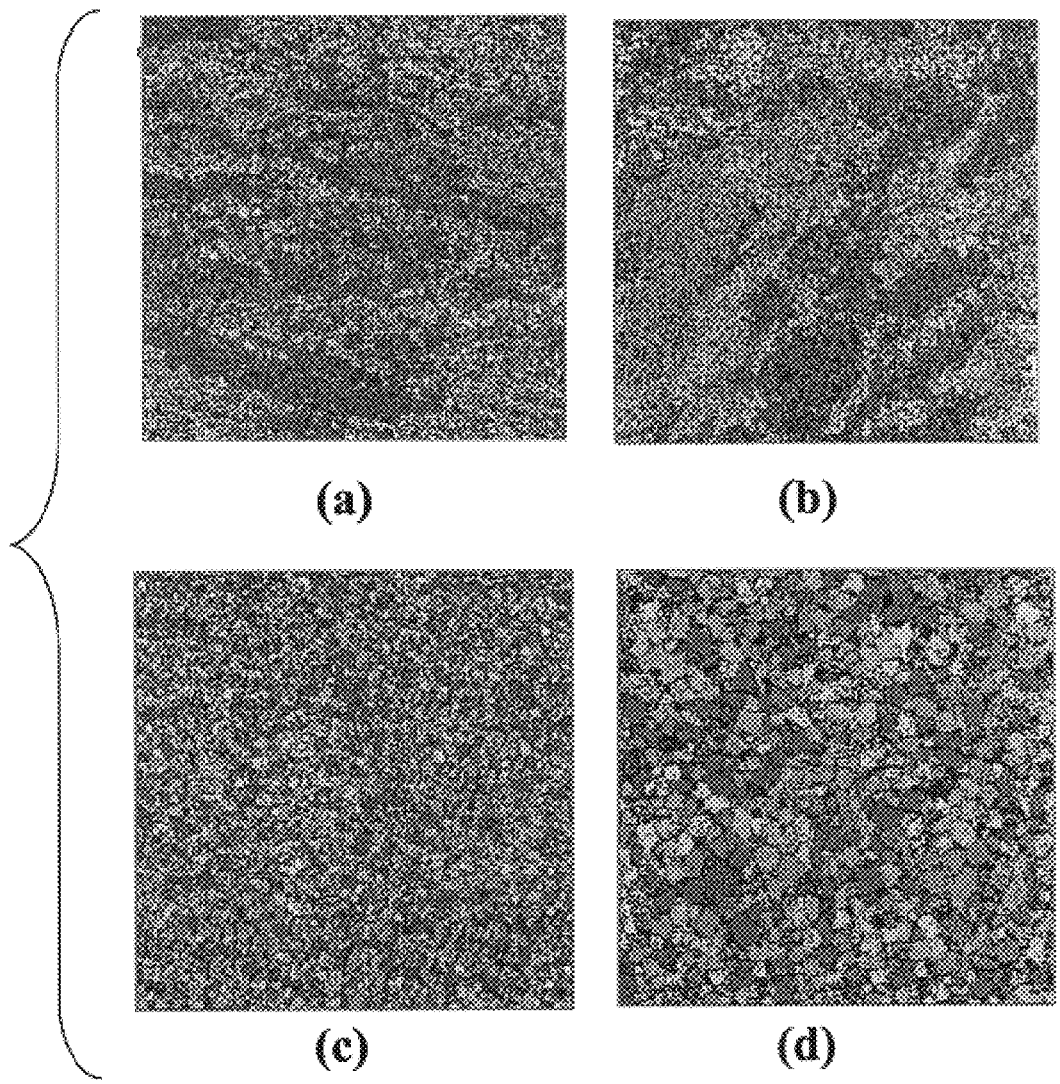
FIG. 2 illustrates icosahedral images generated from EBSP analysis of a Ti6242 material in the following conditions: (a) conventional billet; (b) conventional forging; (c) UFG billet; (d) forged UFG billet.
Figure 3:
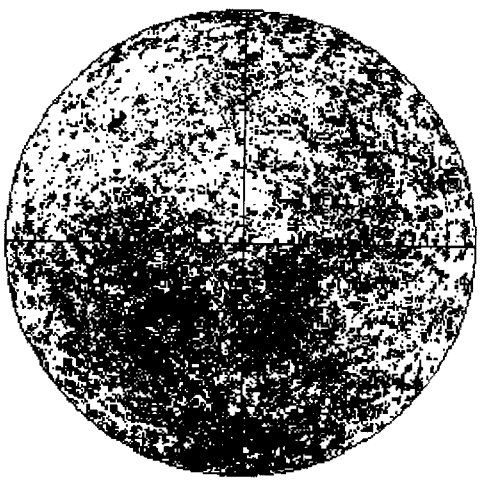
FIG. 3 illustrate [0001] pole figures generated from EBSP analysis of a Ti6242 material in the following conditions: (a) conventional billet; (b) conventional forging; (c) UFG billet; (d) forged UFG billet.
Figure 3:
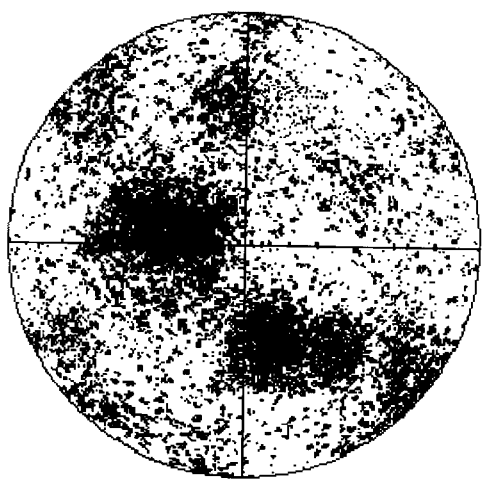
Figure 3:
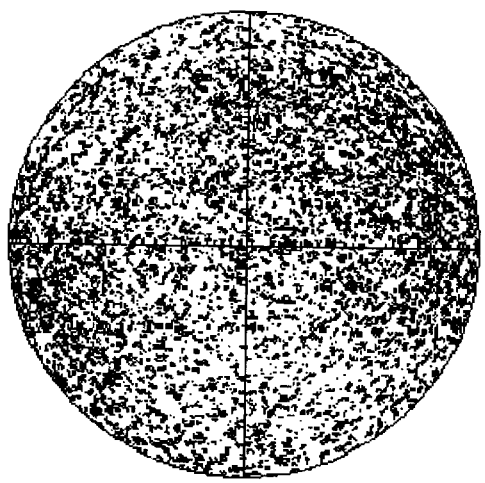
Figure 3:
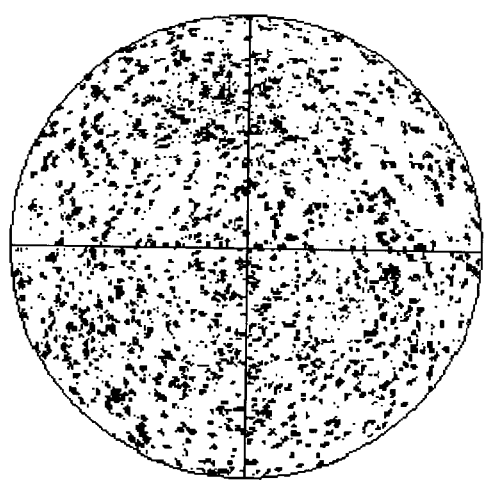

The microstructure of each billet is then evaluated by light microscopy. The crystallographic texture of each billet is then determined by electron backscatter diffraction pattern (EBSP) analysis. Light micrographs for each billet are displayed in FIG. 1, where legend (a) is the conventional billet; legend (b) is the conventional forging; legend (c) is the UFG billet; and legend (d) is the forged UFG billet. FIG. 2 shows EBSP "icosahedral" images, in which the [0001] pole inclination of a scanned microstructure is represented in colors. In FIG. 2, colors that are close to one another on an accepted "20-sided (icosahedral) color sphere" represent microstructure inclinations that are similar in pole inclination. Further, in FIG. 2, a black pixel is a pixel for which no crystallographic orientation can be determined. Further, FIG. 3 shows [0001] pole figures for the regions of the scanned images FIG. 2. The legends for FIGS. 2 and 3 are similar to those of FIG. 1.

As illustrated, the conventional billet microstructure contains primary αTi particles, with a thickness of about 5 $\mu$m, and lengths in a range from about 5 $\mu$m to about 10 $\mu$m, as illustrated in FIG. 1, legend (a). The αTi particles are arranged in colonies, typically about 100 $\mu$m wide and over about 300 $\mu$m long, as illustrated in FIG. 2, legend (a). The αTi phase orientation of the sample scanned in FIG. 2, legend (a) indicate strong crystallographic texture, with most [0001] poles in the lower region of the pole, as illustrated in FIG. 3, legend (a).

The microstructure of the forging from the conventional billet contains primary αTi particles, with diameters in a range from about 5 to about 10 $\mu$m, FIG. 1, legend (b). As illustrated, there appears to be substantial breakup of the billet microstructure. αTi particles are arranged in large colonies comprising similar crystallographic orientations. For example, some αTi colonies are about 300 $\mu$m wide and often greater than about 1000 $\mu$m long, as illustrated in FIG. 2, legend (b). The αTi phase orientation of the sample scanned in FIG. 2, legend (b) has strong crystallographic texture, meaning that a majority of the [0001] poles are grouped within two regions of the pole figure, as illustrated in FIG. 3, legend (b). This strong grouping of the poles suggests that the scanned region comprises two colonies.

The ultrasonic inspection of the UFG billet indicates a microstructure comprising αTi particles. The particles comprise diameters about 5 $\mu$m, as illustrated in FIG. 1, legend (c). These αTi particles do not appear to be provided in colonies, as illustrated in FIG. 2, legend (c). The αTi phase orientation of the sample scanned as illustrated in FIG. 2, legend (c) appears random, as illustrated in FIG. 3, legend (c).

The microstructure of the heat-treated forging of the UFG billet indicates that it comprises αTi particles. The αTi particles have diameters about 10 μm, as illustrated in FIG. 1, legend (d). These αTi particles are larger than the billet from which the αTi particles are formed, and this suggests grain growth during at least one of forging or heat treatment of the UFG billet. The αTi particles are not provided in colonies, as illustrated in FIG. 2, legend (d). The αTi phase orientation appears random, as illustrated in FIG. 3, legend (d).

The ultrasonic characteristics of the billets formed different titanium articles and structures are determined by C-scans of blocks formed from billets of the titanium articles and structures. The titanium articles and structures are provided as blocks about 0.79 mm (1/32 inch) diameter flat bottom holes. The titanium blocks are formed about 38 mm thick with holes drilled to about 25 mm below top surface of the block. Each of the conventional billet, conventional forging, and UFG billet have surface dimensions about 64 millimeters (mm) square, and each also has 9 flat bottom holes. The forging made from the UFG material had dimensions about 64 mm by about 28 mm, and is provided with 6 flat bottom holes. Each titanium block is machined with sufficient orientations so that an ultrasonic inspection direction is similar to that of a larger component formed from the titanium articles and structures. For example, the 38 mm thickness of the titanium block is disposed in the radial direction of the billet or forging.

The ultrasonic transducers used for the ultrasonic inspection by C-scanning processes are listed in Table 1. Table 1 also provides characteristics of the ultrasonic transducers. The transducers comprise polyvinylidine fluoride (PVDF) as a piezoelectric element. Center frequencies for the ultrasonic transducers are measured from signals reflected off the backwall of a fused silica block.

TABLE 1

Characteristics of Transducers

| Transducer | Nominal Frequency | Actual Frequency | Diameter | Focal Length | Aperture |
|---|---|---|---|---|---|
| 1 | 5 MHz | 6.62 MH | 19 mm | 133 mm | f/7 |
| 2 | 10 MHz | 11.36 MH | 19 mm | 133 mm | f/7 |
| 3 | 20 MHz | 18.43 MH | 19 mm | 133 mm | f/7 |

Two separate series of water immersion ultrasonic C-scans were performed on the titanium-containing blocks. The series of water immersion ultrasonic C-scans were performed at nominal frequencies of about 5 MHz about 10 MHz, and 20 MHz. One scan at each of the above-frequencies is performed to measure a signal from the flat bottom holes. A second scan at each of the above-frequencies is performed at a higher amplification to get noise and sound scattering sensitivity statistics.

Each of the scans is made over a square region about 147.5 mm in length and width, with about a 0.144 mm scan and index increment. The sound is focused about 25 mm below the top surface of the blocks, which is disposed in the approximate the plane of the flat bottom holes. The width of scan signal gate is about 4 microseconds. The obtained C-scan images are about 1024 pixels by about 1024 pixels.

Figure 4:
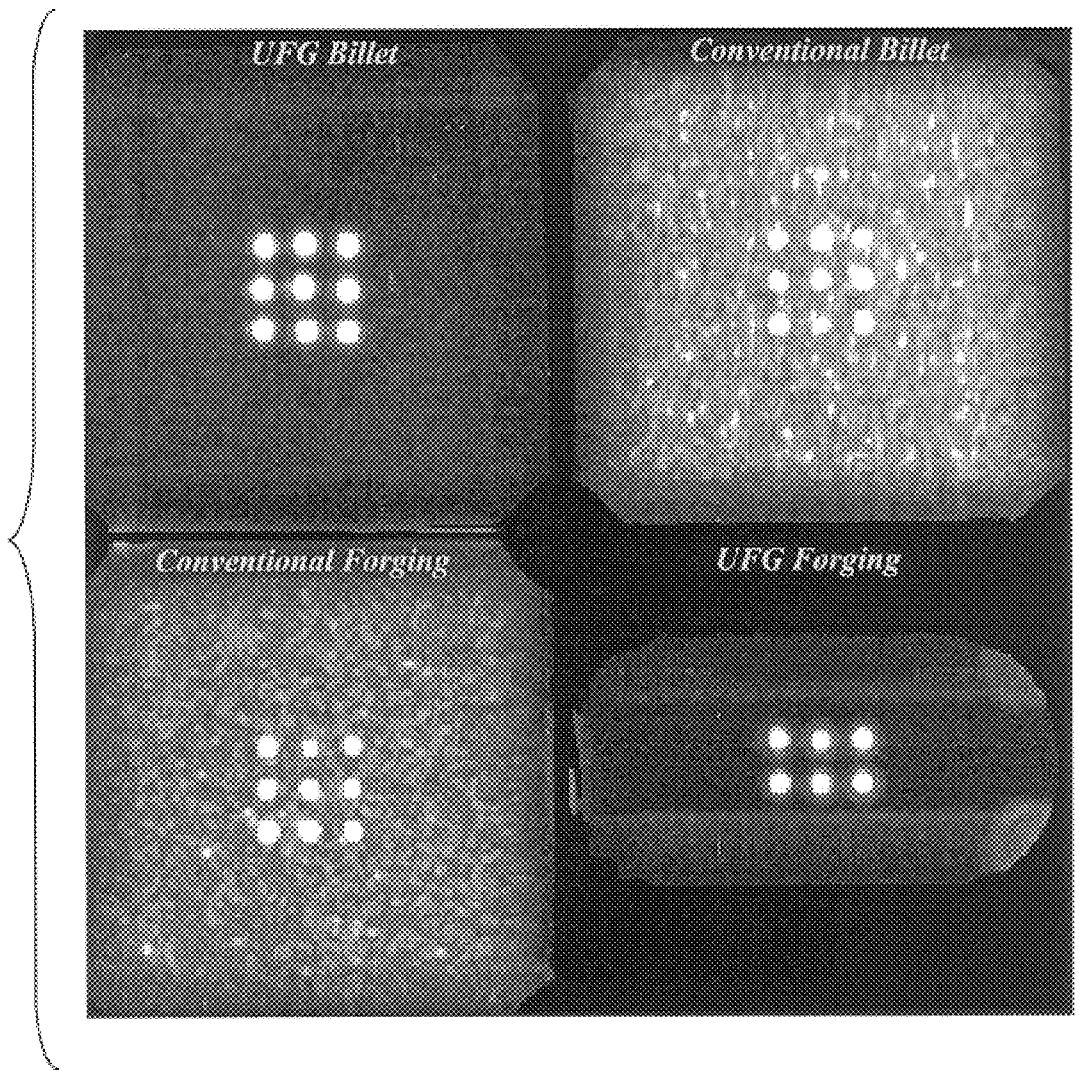
FIG. 4 illustrate 5 MHz C-scan images of Ti6242 blocks containing arrays of 0.79 mm (1/32 inch) diameter flat bottom holes, which are drilled 25 mm below a surface, in which the top left is titanium UFG billet, the top right is a conventional titanium billet, the bottom left is a conventional titanium forging, and the bottom right is a titanium UFG forging, whereing the 5 MHz C-scan images are taken at 12 dB attenuation noise scan.

FIG. 4, legends (a)–(d), illustrate C-scan images made at about 5 MHz. With reference to FIG. 4, the UFG billet material is in the upper left, the conventional billet is on the upper right, the conventional forging is on the lower left, and the forging of the UFG material is on the lower right. The conventional billet and forging exhibit a higher background noise, as indicated by brighter pixels in those blocks as illustrated in FIG. 4, legend (a). A lower intensity is exhibited from the flat bottom holes, as indicated by a lower intensity of pixels from those regions as illustrated in FIG. 4, legend (b).

Quantitative measures of signal and noise can then be determined from the C-scans. The signal from each flat bottom hole is taken as the brightest pixel within the 3×3 array of the nine brightest pixels. Noise statistics and sound scattering sensitivity can then be determined from square pixel arrays that did not comprise the flat bottom holes. The quantitative data is presented in Table 2. In Table 2, a signal is an average signal from all flat bottom holes in the respective block. The signal to noise ratios are calculated both as:

(Average Signal−Average Noise)÷(Maximum Noise−Average Noise) as well as:

(Average Signal−Average Noise)÷(3 $\rho_{Noise}$).

TABLE 2

Ultrasonic Signals and Noise Measurements in Ti6242 Blocks

| | | FBH Signals | | Noise | | | |
|---|---|---|---|---|---|---|---|
| Material | MHz | Attenuation dB | S | Attenuation dB | $N_{ave}$ | $N_{max}$ | $\sigma_{noise}$ |
| Conventional billet | 6.62 | −34 | 94.4 | −12 | 61.3 | 141 | 11.1 |
| Conventional, forged | 6.62 | −34 | 53.4 | −12 | 44.7 | 107.5 | 9.48 |
| UFG billet | 6.62 | −34 | 216.1 | −12 | 9.1 | 34.5 | 1.70 |
| UFG, forged | 6.62 | −34 | 108.5 | −12 | 4.3 | 12.5 | 0.973 |
| Conventional billet | 11.36 | −49 | 75.4 | −12.5 | 130.9 | 243.5 | 21.5 |
| Conventional, forged | 11.36 | −49 | 42.7 | −12.5 | 81.8 | 249.5 | 17.2 |
| UFG billet | 11.36 | −49 | 214.5 | −12.5 | 23.1 | 59.5 | 4.38 |
| UFG, forged | 11.36 | −49 | 100.5 | −12.5 | 5.9 | 11.5 | 1.11 |
| Conventional billet | 18.43 | −48.5 | 51.3 | −10 | 73.6 | 168.5 | 12.4 |
| Conventional, forged | 18.43 | −48.5 | 20.4 | −10 | 38.8 | 142.5 | 8.35 |
| UFG billet | 18.43 | −48.5 | 212.2 | −10 | 21.5 | 71.5 | 4.11 |
| UFG, forged | 18.43 | −48.5 | 93.5 | −10 | 11.9 | 20.5 | 1.40 |

The determined signal to noise ratio calculations, as embodied by the invention, are listed in Table 3. Both calculation methods, as described above, provide a measure of a signal's intensity in a selected block relative to noise spikes in the same block.

TABLE 3

Signal to Noise Ratio in Ti6242 Blocks

| | | Signal to Noise Ratio | |
|---|---|---|---|
| Material | MHz | $(S_{ave}-N_{ave})/(N_{Max}-N_{ave})$ | $(S_{ave}-N_{ave})/3\sigma_{noise}$ |
| Conventional billet | 6.62 | 14.2 | 33.9 |
| Conventional, forged | 6.62 | 10.0 | 22.0 |
| UFG billet | 6.62 | 106.7 | 531.3 |
| UFG, forged | 6.62 | 166.6 | 466.4 |
| Conventional billet | 11.36 | 43.6 | 76.1 |
| Conventional, forged | 11.36 | 16.5 | 53.7 |
| UFG billet | 11.36 | 393.7 | 1089.8 |
| UFG, forged | 11.36 | 1195.2 | 2015.7 |
| Conventional billet | 18.43 | 44.7 | 113.8 |

TABLE 3-continued

Signal to Noise Ratio in Ti6242 Blocks

| Material | MHz | Signal to Noise Ratio $(S_{ave}-N_{ave})/(N_{Max}-N_{ave})$ | $(S_{ave}-N_{ave})/3\sigma_{noise}$ |
|---|---|---|---|
| Conventional, forged | 18.43 | 16.2 | 67.0 |
| UFG billet | 18.43 | 356.7 | 1445.5 |
| UFG, forged | 18.43 | 915.0 | 1873.2 |

Accordingly, if the determining a signal to noise ratio level is conducted by (Average Signal−Average Noise)÷(Maximum Noise−Average Noise), it can be generalized that the material comprises uniform fine grains at 6.62 MHz if the a signal to noise ratio—for a signal from 0.79 mm (1/32 inch) diameter flat bottom holes 25 mm below the inspected surface of the material—is at least about 20; at 11.36 MHz a signal to noise ratio level is at least about 50; and at 18.43 MHz a signal to noise ratio level is at least about 50. Further, if the determining a signal to noise ratio level is conducted by (Average Signal−Average Noise)÷(3 $\sigma_{Noise}$) for the subject flat bottom holes, it can be also generalized that the material comprises uniform fine grains at 6.62 MHz if the a signal to noise ratio level is at least about 50; at 11.36 MHz a signal to noise ratio level is at least about 100; and at 18.43 MHz a signal to noise ratio level is at least about 150. Each of these signal to noise ratio levels correspond to a preset noise level as determined by the pre-drilled holes in the material.

Figure 6:
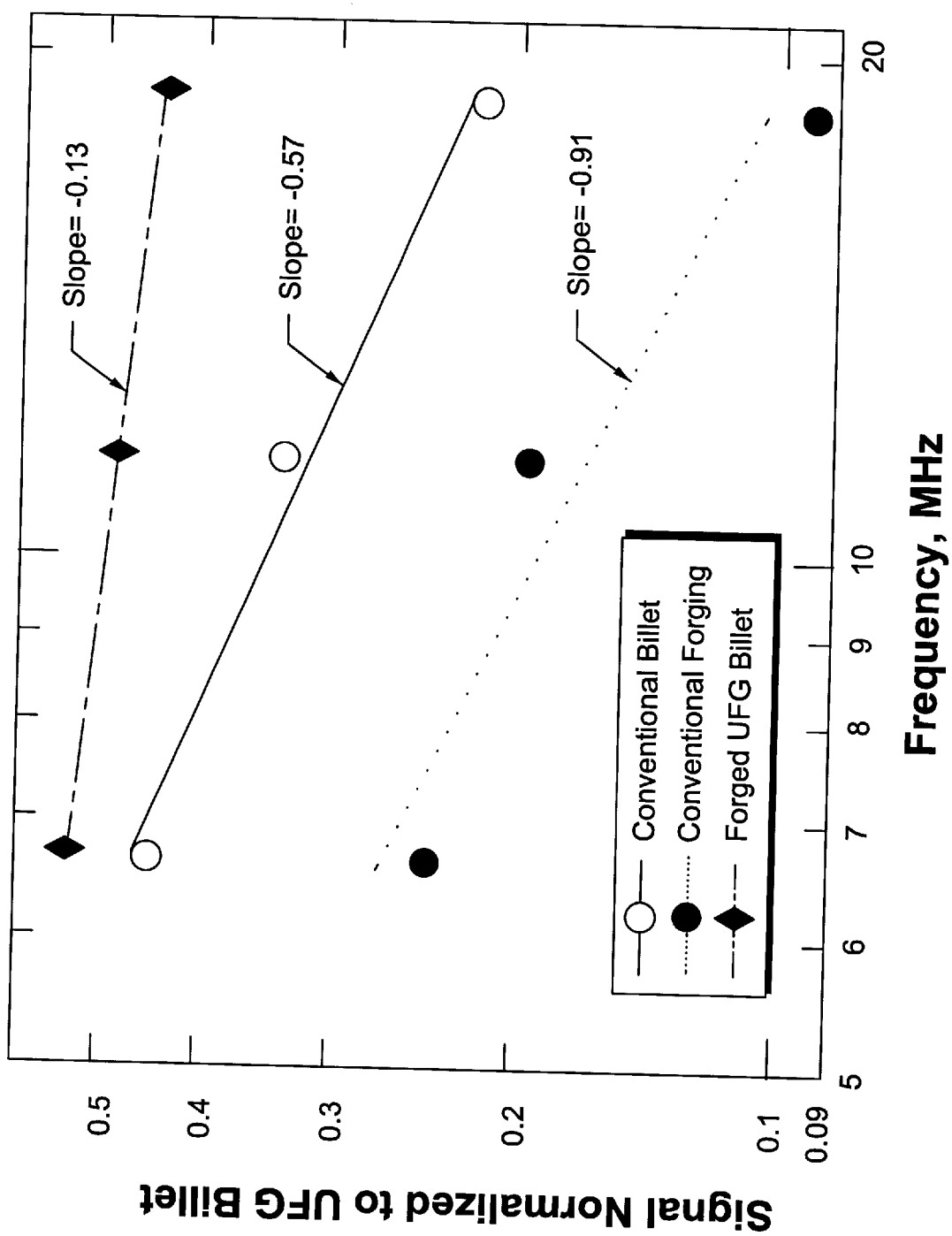
FIG. 6 illustrates a graph of average signals from flat bottom holes with respect to those in the block machined from the conventional billet.
Figure 7:
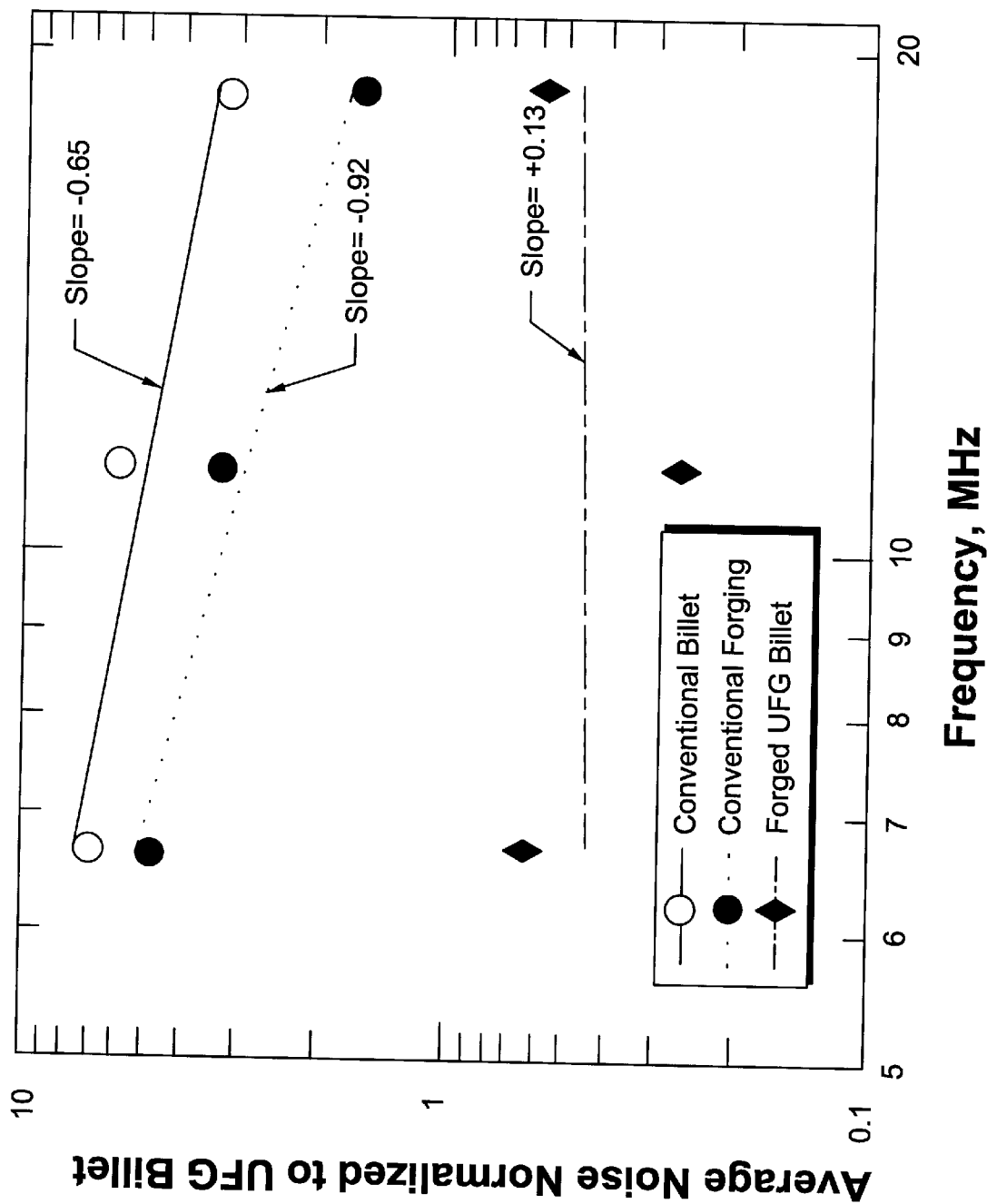
FIG. 7 illustrates a graph of average noise from blocks referenced to that from the block machined from the conventional billet.
Figure 8:
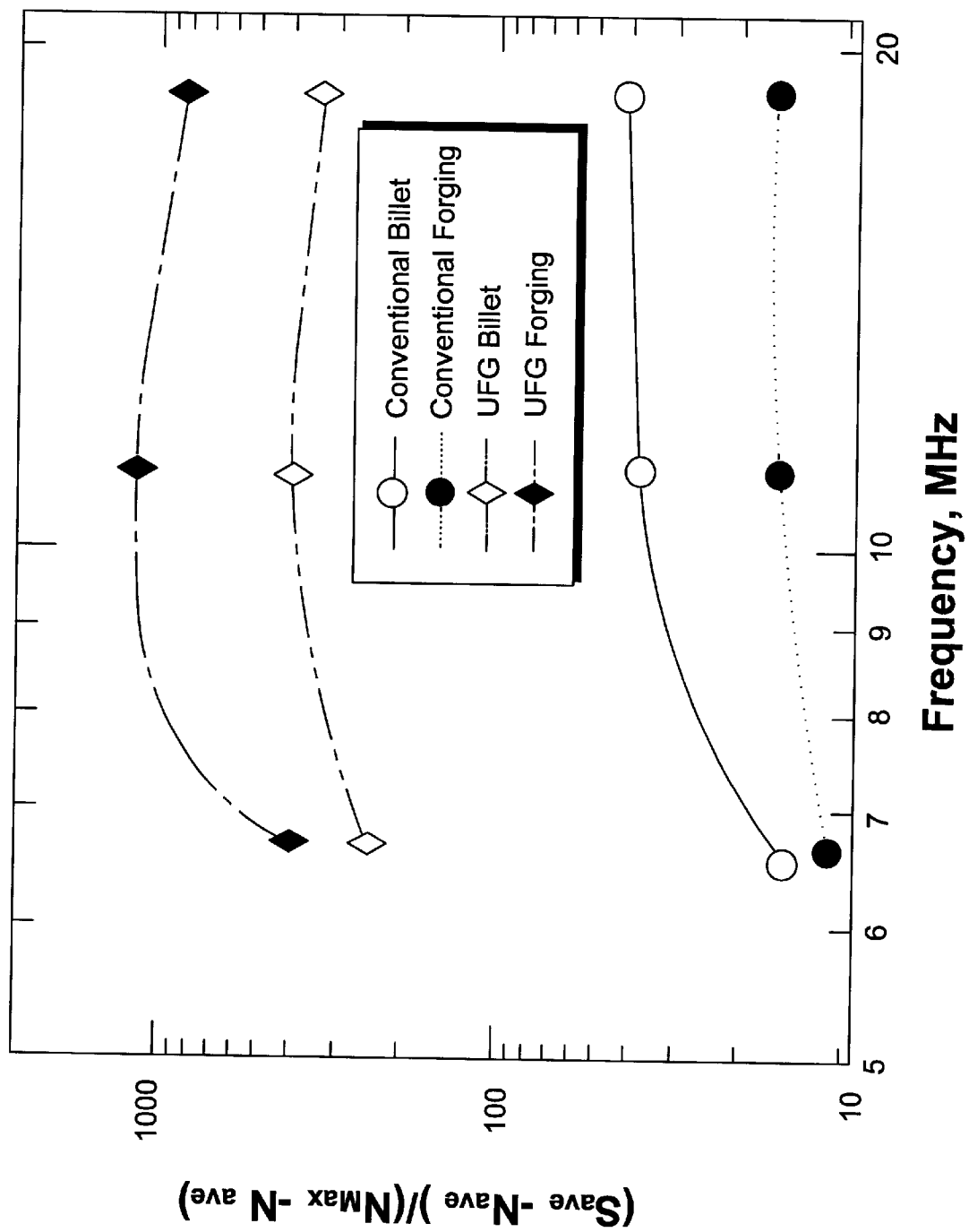
FIG. 8 illustrates a graph of signal to noise ratios of Ti6242 blocks as a function of frequency.

The highest signal from flat bottom holes is measured in the UFG billet, and the lowest signal from flat bottom holes is measured in a conventional forging, as illustrated in the graph of FIG. 6. The highest average noise, the largest maximum noise, and the largest standard deviation of noise are measured in a conventional billet. The lowest average noise, the smallest maximum noise, and the smallest standard deviation of noise are measured in a forging of UFG material, as illustrated in the graph of FIG. 7. Accordingly, it can be determined that the forged UFG material possesses the highest signal to noise ratio, and that the conventional forging had the lowest signal to noise ratio, as illustrated in the graph of FIG. 8.

In the ultrasonic inspection of the titanium articles and structures, as embodied by the invention, longitudinal sound velocities were measured in a Ti6242 extrusion. The Ti6242 extrusion was processed to create a strong [0001] texture in the direction of extrusion. For example, the extrusion of the Ti6242 is performed at about 1040° C. and a ratio of about 8:1. The extrusion is then heat treated at about 593° C. for about 8 hours. X-ray investigation and analysis determine the grain and microstructure orientation of the Ti6242. This investigation and analysis of the Ti6242 indicates a strong [0001] texture along the extrusion direction, with [0001] intensity along the extrusion direction. The intensity has been determined to be about 22 times random.

The ultrasonic behavior of small titanium articles and structures, for example a Ti6242 alloy, can be determined by ultrasonic inspection of the titanium articles and structures as a function of ultrasonic frequency and material microstructure. The speed of sound in αTi is about 6 mm/μs. At an ultrasonic frequency of 5 MHz, the wavelength is about 1.2 mm in the titanium articles and structures. Colony sizes greater than about 200 μm could change the scattering character from Rayleigh toward stochastic (phase). Sound velocities in the Ti6242 are measured on rectangular Ti6242 pieces that are formed from the respective Ti6242 billets. The rectangular Ti6242 pieces are about 16 mm long in the extrusion direction and about 12 mm in length in a direction normal to the extrusion direction. Longitudinal velocity is measured at about 10 MHz with a contact transducer, amplifier, and oscilloscope. The longitudinal velocity is determined by measuring a time for a sound pulse to travel down the selected direction and return. The sound velocity along the extrusion direction is about 6.28 mm/μs; while the sound velocity in a direction normal to the extrusion direction is about 6.10 mm/μs.

The results from the ultrasonic inspection and the determination of the titanium articles and structures, along with microstructure characteristic of the titanium articles and structures are based on UFG billet blocks, which are formed from conventional billet material, as described above. The UFG process produces samples in which the original αTi colony structure in the conventional billet is eliminated. The steps of forging the UFG material at about 900° C. and with a corresponding about a 60% height reduction did not re-create αTi colonies or develop strong texture and αTi microstructure.

Figure 5:
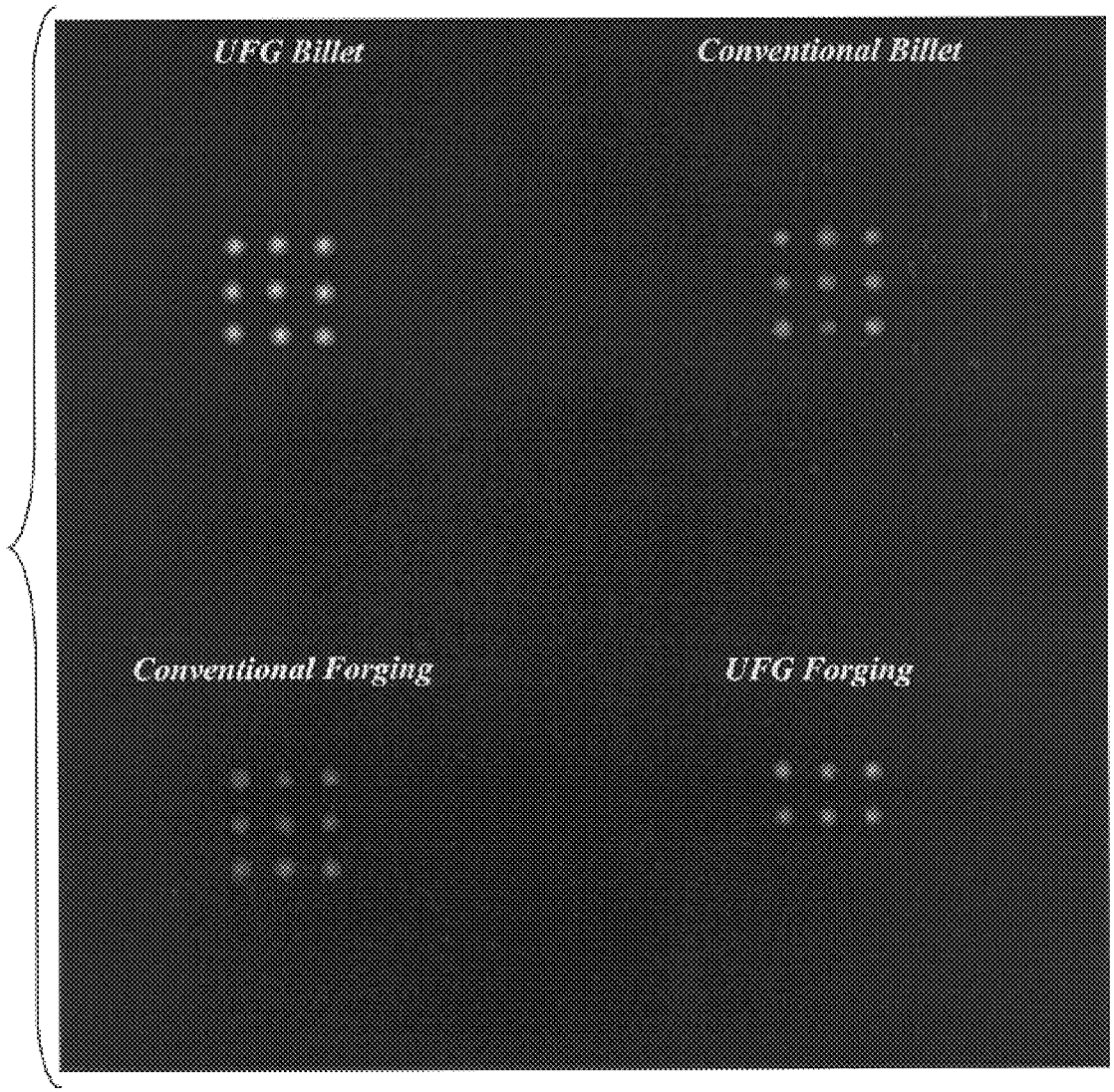
FIG. 5 illustrate 5 MHz C-scan images of Ti6242 blocks containing arrays of 0.79 mm (1/32 inch) diameter flat bottom holes, which are drilled 25 mm below a surface, in which the top left is titanium UFG billet, the top right is a conventional titanium billet, the bottom left is a conventional titanium forging, and the bottom right is a titanium UFG forging, wherein the 5 MHz C-scan images are taken at 34 dB attenuation signal scan.

With reference to FIGS. 6 and 7, differences in sound scattering sensitivity and noise are illustrated to be generally dependent on frequency. This dependency suggests that a scattering entity size, such as the size of a colony, in the conventional material increases the contribution to scattering, sound scattering sensitivity, and attenuation from phase scattering. This change in contribution is not a complete shift from one pure scattering mechanism to the other scattering mechanism, such as a Rayleigh scattering mechanism to a phase scattering mechanism, since such a shift would give a slope of about −2 in FIG. 5.

The αTi particle size is generally not significant in any determining of a signal to noise ratio, since the αTi particle sizes are similar in all materials and are generally smaller in size than the ultrasonic wavelength. A difference in the various material, in the ultrasonic inspection, as embodied by the invention, comprises a presence of large colonies in conventional billets and forgings. Noting this difference, the speed of sound in Ti6242 extrusion samples is about 6 mm/μs. This speed typically corresponds to ultrasonic inspection wavelengths of about 1.2 mm at about 5 MHz, about 600 μm at about 10 MHz, and about 300 μm at about 20 MHz. Therefore, the colony dimensions in the conventional billet and forging are comparable to the ultrasonic wavelength.

The relative contributions of Rayleigh scattering and phase scattering are frequency dependent, for example in the ultrasonic frequency range. The frequency dependency is due, at least in part, to the 18.43 wavelength of about 300 μm being about the size of a αTi colony thickness. The 6.62 MHz wavelength of about 900 μm is about 3 times a αTi colony size. Scattering at 6.62 MHz enters the phase scattering region for its contribution, while scattering at 18.43 MHz provides substantial phase scattering contributions.

The UFG forged material results in a slightly larger grain size than the original billet. However, UFG forged material possesses a lower noise and higher signal, as indicated in Table 2. This behavior may be due to a slightly lower volume fraction of αTi particles in the forged material, which is illustrated in FIG. 1, legends (c) and (d).

The conventional forging possesses a lower noise than a conventional billet, however, has a lower signal to noise ratio, which may be due in part to low signals from the flat bottom holes. The conventional forging has a lower volume fraction of αTi particles than the billet. The lower signal in the conventional forging may be caused by attenuation due, at least in part, to sound traveling along highly textured regions. The dimensions of the reflecting entity αTi colonies up to about 1 mm in length and about 300 μm in width in the conventional billet and forging may result in a stochastic (phase) component to the resultant scattering. It is also possible that a αTi colony structure above the flat bottom holes scatters the reflection from the flat bottom holes.

The microstructures of UFG billets and forgings made from UFG billets comprise fine-scale granular αTi particles. These αTi particles are generally less than about 5 μm in diameter, and are generally provided with an absence of crystallographic texture. Ultrasonic inspectability, which is characterized by signal to noise ratio from machined flat bottom holes, is greater in the UFG materials than in the conventional materials. There is less ultrasonic backscattered noise in the UFG materials than there is in the conventional materials. Further, the ultrasonic signal from machined flat bottomed holes is higher in the UFG material.

The presence of αTi colony structure is associated with ultrasonic noise generated by ultrasonic inspection of titanium articles and structures, as embodied by the invention. For materials with αTi particles less than about 10 μm in size, differences in αTi particle size typically do not have a significant effect on generated ultrasonic noise. For example, UFG billets, as embodied by the invention, display chiefly Rayleigh scattering, while conventional billets, which can not be characterized by UFG properties, display Rayleigh scattering plus phase scattering. The inspectability of titanium-containing materials is enhanced with predominantly Rayleigh scattering.

While various embodiments are described herein, it will be appreciated from the specification that various combinations of elements, variations or improvements therein may be made by those skilled in the art, and are within the scope of the invention.

What is claimed is:

1. An ultrasonically inspectable titanium article, said ultrasonically inspectable titanium article comprising:
    a) a uniform fine grain microstructure that scatters ultrasonic radiation having a predetermined wavelength by Rayleigh-type scattering;
    b) a plurality of αTi particles, said plurality of αTi particles being arranged in a plurality of αTi colonies and randomly oriented with respect to each other, wherein each of said αTi colonies has a diameter that is less than said wavelength.

2. The ultrasonically inspectable titanium article of claim 1, wherein said diameter of each of said plurality of αTi colonies is less than about ¼ of said wavelength.

3. The ultrasonically inspectable titanium article of claim 1, wherein each of said plurality of αTi particles has a diameter of less than about 5 microns.

4. The ultrasonically inspectable titanium article of claim 1, wherein said ultrasonically inspectable titanium article is a billet.

5. The ultrasonically inspectable titanium article of claim 4, wherein said billet is a heat treated forged billet, and wherein each of said plurality of αTi particles has a diameter of less than about 10 microns.

6. The ultrasonically inspectable titanium article of claim 1, wherein said titanium article is a forging.

7. An ultrasonically inspectable titanium article, said titanium article comprising a plurality of αTi particles, said plurality of αTi particles being arranged in a plurality of αTi colonies and randomly oriented with respect to each other, and having at least one synthetic flaw that scatters said ultrasonic radiation having a predetermined wavelength such that ultrasonic radiation scattered at a predetermined frequency by said synthetic flaw has a signal-to-noise ratio that is greater than a predetermined signal-to-noise ratio.

8. The ultrasonically inspectable titanium article of claim 7, wherein said synthetic flaw comprises a plurality of flat-bottomed holes in a face of said titanium article.

9. The ultrasonically inspectable titanium article of claim 8, wherein said plurality of flat-bottomed holes comprises two rows of three flat-bottomed holes.

10. The ultrasonically inspectable titanium article of claim 7, wherein said signal-to-noise ratio is determined by dividing the difference between an average signal value and an average noise value by the difference between a maximum noise value and the average signal value, and wherein said predetermined frequency is about 6 MHz and said predetermined signal-to-noise ratio is greater than about 20.

11. The ultrasonically inspectable titanium article of claim 7, wherein said signal-to-noise ratio is determined by dividing the difference between an avenge signal value and an average noise value by the difference between a maximum noise value and the average signal value, and wherein said predetermined frequency is about 11 MHz and said predetermined signal-to-noise ratio is greater than about 20.

12. The ultrasonically inspectable titanium article of claim 7, wherein said signal-to-noise ratio is determined by dividing the difference between an average signal value and an average noise value by the difference between a maximum noise value and the avenge signal value, and wherein said predetermined frequency is about 18 MHz and said predetermined signal-to-noise ratio is greater than about 50.

13. An ultrasonically inspectable titanium article, said ultrasonically inspectable titanium article comprising:
    a) a uniform fine grain microstructure that scatters said ultrasonic radiation by Rayleigh-type scattering;
    b) a plurality of αTi particles, said plurality of αTi particles being randomly oriented with respect to each other and arranged in a plurality of αTi colonies, wherein each of said αTi colonies has a diameter that is less than said wavelength; and
    c) at least one synthetic flaw that scatters said ultrasonic radiation such that ultrasonic radiation scattered at a predetermined frequency by said synthetic flaw has a signal-to-noise ratio that is greater than a predetermined signal-to-noise ratio.

14. The ultrasonically inspectable titanium article of claim 13, wherein said diameter of each of said plurality of αTi colonies is less than about ¼ of said wavelength.

15. The ultrasonically inspectable titanium article of claim 13, wherein each of said plurality of αTi particles has a diameter of less than about 5 microns.

16. The ultrasonically inspectable titanium article of claim 13, wherein said ultrasonically inspectable titanium article is a billet.

17. The ultrasonically inspectable titanium article of claim 16, wherein said billet is a heat treated forged billet, and wherein each of said plurality of αTi particles has a diameter of less than about 10 microns.

18. The ultrasonically inspectable titanium article of claim 13, wherein said titanium article is a forging.

19. The ultrasonically inspectable titanium article of claim 13, wherein said synthetic flaw comprises a plurality of flat-bottomed holes in a face of said titanium article.

20. The ultrasonically inspectable titanium article of claim 19, wherein said plurality of flat-bottomed holes comprises two rows of three flat-bottomed holes.

21. The ultrasonically inspectable titanium article of claim 13, wherein said signal-to-noise ratio is determined by dividing the difference between an average signal value and an average noise value by the difference between a maximum noise value and the average signal value, and wherein said predetermined frequency is about 6 MHz and said predetermined signal-to-noise ratio is greater than about 20.

22. The ultrasonically inspectable titanium article of claim 13, wherein said signal-to-noise ratio is determined by dividing the difference between an average signal value and an average noise value by the difference between a maximum noise value and the average signal value, and wherein said predetermined frequency is about 11 MHz and said predetermined signal-to-noise ratio is greater than about 20.

23. The ultrasonically inspectable titanium article of claim 13, wherein said signal-to-noise ratio is determined by dividing the difference between an average signal value and an average noise value by the difference between a maximum noise value and the average signal value, and wherein said predetermined frequency is about 18 MHz and said predetermined signal-to-noise ratio is greater than about 50.

24. A method of making a uniformly fine grain ultrasonically inspectable titanium billet comprising a uniformly fine grain microstructure and a plurality of αTi particles randomly oriented with respect to each other and arranged in a plurality of αTi colonies, wherein each of the αTi colonies has a diameter that is less than a predetermined wavelength of scattered ultrasonic radiation, the method comprising the steps of:

a) providing an ultra-fine grain titanium billet;
b) press forging the billet at about 900° C.;
c) heat treating the billet at about 970° C. for about one hour;
d) helium quenching the billet at about 705° C. for about eight hours; and
e) air-cooling the billet, thereby forming the uniformly fine grain ultrasonically inspectable titanium billet.

* * * * *